United States Patent
LeBrun-Blashka et al.

(10) Patent No.: US 10,751,362 B2
(45) Date of Patent: Aug. 25, 2020

(54) COMPOSITIONS AND METHODS FOR MANAGING DIGESTIVE DISORDERS AND A HEALTHY MICROBIOME

(71) Applicant: Metagenics, Inc., Aliso Viejo, CA (US)

(72) Inventors: Sara LeBrun-Blashka, Grafton, WI (US); John Troup, Aliso Viejo, CA (US); Nikhat Contractor, Aliso Viejo, CA (US)

(73) Assignee: METAGENICS, INC., Aliso Viejo, CA (US)

( * ) Notice: Subject to any disclaimer, the term of this patent is extended or adjusted under 35 U.S.C. 154(b) by 0 days.

(21) Appl. No.: 15/651,108

(22) Filed: Jul. 17, 2017

(65) Prior Publication Data

US 2018/0015032 A1    Jan. 18, 2018

Related U.S. Application Data

(60) Provisional application No. 62/363,590, filed on Jul. 18, 2016.

(51) Int. Cl.
| | |
|---|---|
| *A61K 31/715* | (2006.01) |
| *A61K 31/702* | (2006.01) |
| *A23L 33/00* | (2016.01) |
| *A23L 33/16* | (2016.01) |
| *A23L 33/115* | (2016.01) |
| *A23K 20/158* | (2016.01) |
| *A23L 33/17* | (2016.01) |
| *A23L 33/15* | (2016.01) |
| *A23L 33/175* | (2016.01) |
| *A23L 33/18* | (2016.01) |
| *A23K 20/174* | (2016.01) |
| *A23K 20/20* | (2016.01) |
| *A23K 20/142* | (2016.01) |
| *A23L 33/21* | (2016.01) |
| *A23L 2/52* | (2006.01) |
| *A61K 9/00* | (2006.01) |
| *A61K 31/07* | (2006.01) |
| *A61K 31/197* | (2006.01) |

(Continued)

(52) U.S. Cl.
CPC .......... *A61K 31/715* (2013.01); *A23K 20/142* (2016.05); *A23K 20/158* (2016.05); *A23K 20/174* (2016.05); *A23K 20/20* (2016.05); *A23L 2/52* (2013.01); *A23L 33/115* (2016.08); *A23L 33/15* (2016.08); *A23L 33/16* (2016.08); *A23L 33/17* (2016.08); *A23L 33/175* (2016.08); *A23L 33/18* (2016.08); *A23L 33/21* (2016.08); *A23L 33/40* (2016.08); *A61K 9/0056* (2013.01); *A61K 9/0095* (2013.01); *A61K 31/07* (2013.01); *A61K 31/197* (2013.01); *A61K 31/198* (2013.01); *A61K 31/28* (2013.01); *A61K 31/355* (2013.01); *A61K 31/375* (2013.01); *A61K 31/401* (2013.01); *A61K 31/405* (2013.01); *A61K 31/4172* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/555* (2013.01); *A61K 31/593* (2013.01); *A61K 31/702* (2013.01); *A61K 31/7016* (2013.01); *A61K 31/714* (2013.01); *A61K 33/18* (2013.01); *A61K 33/30* (2013.01); *A61K 33/32* (2013.01); *A61K 33/34* (2013.01); *A61K 38/168* (2013.01); *A61K 45/06* (2013.01); *A23V 2002/00* (2013.01)

(58) Field of Classification Search
None
See application file for complete search history.

(56) References Cited

U.S. PATENT DOCUMENTS

2004/0235789 A1*  11/2004  Day ............... A61K 31/715
                                                  514/54
2006/0165670 A1    7/2006  Beer et al.
(Continued)

FOREIGN PATENT DOCUMENTS

| CN | 102366615 A | 3/2012 |
| EP | 2827724 A1 | 1/2015 |

OTHER PUBLICATIONS

Ruiz-Matute, A.I. et al.; "Gas chromatographic-mass spectrometric characterisation of tri- and tetrasaccharides in honey."; Elsevier, Food Chemistry 120, pp. 673-642; Published May 15, 2010.

(Continued)

*Primary Examiner* — Dale R Miller
(74) *Attorney, Agent, or Firm* — Warner Norcross + Judd LLP

(57) ABSTRACT

Disclosed is a prebiotic composition comprising a combination of 2'fucosyllactose (2'FL) and isomaltooligosaccharide (IMO). The 2'FL and IMO are present in the prebiotic composition in a weight ratio of from 1:1 to 1:10. The prebiotic composition is effective for use in methods of preventing and/or treating a gastrointestinal (GI) condition in an animal, such as irritable bowel syndrome (IBS), inflammatory bowel disease(s) (IBD), Crohn's disease, and ulcerative colitis (UC). A foodstuff or beverage, a medical food, a nutritional composition, and a kit presentation, each including the prebiotic composition, and each suitable for use in methods of reducing or suppressing inflammation in an animalian tract, are also disclosed. A method of using the prebiotic composition to prevent and/or treat a GI condition in an animal is further disclosed. The method comprises administering the prebiotic composition to the animal.

23 Claims, 3 Drawing Sheets

(51) Int. Cl.

| | |
|---|---|
| A61K 31/198 | (2006.01) |
| A61K 31/28 | (2006.01) |
| A61K 31/355 | (2006.01) |
| A61K 31/375 | (2006.01) |
| A61K 31/401 | (2006.01) |
| A61K 31/405 | (2006.01) |
| A61K 31/4172 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/525 | (2006.01) |
| A61K 31/555 | (2006.01) |
| A61K 31/593 | (2006.01) |
| A61K 31/7016 | (2006.01) |
| A61K 31/714 | (2006.01) |
| A61K 33/18 | (2006.01) |
| A61K 33/30 | (2006.01) |
| A61K 33/32 | (2006.01) |
| A61K 33/34 | (2006.01) |
| A61K 38/16 | (2006.01) |
| A61K 45/06 | (2006.01) |

(56) References Cited

U.S. PATENT DOCUMENTS

| | | | | |
|---|---|---|---|---|
| 2012/0171165 | A1* | 7/2012 | Buck | A61K 31/702 514/23 |
| 2012/0294840 | A1* | 11/2012 | Newburg | C07H 3/06 424/93.44 |
| 2013/0336931 | A1* | 12/2013 | Wadstrom | A23L 33/125 424/93.3 |

OTHER PUBLICATIONS

Sprenger, Norbert et al.; "Longitudinal change of selected human milk oligosaccharides and association to infants' growth, an observatory, single center, longitudinal cohort study."; PLoS ONE 12(2): e0171814; DOI: 10.1371/journal.pone.0171814; Published Feb. 9, 2017.

Zhuo-Teng, Yu et al.; "The principal fucosylated oligasaccharides of human milk exhibit prebiotic properties on cultured infant microbiota."; Oxford University Press, Glycobiology 23(2), pp. 169-177; DOI: 10.1093/glycob/cws138; Published Oct. 1, 2012.

Fernandez, Javier et al.; "Colon microbiota fermentation of dietary prebiotics towards short-chain fatty acids and their roles as anti-inflammatory and antitumour agents: A review." Elsevier, Journal of Functional Foods 25, pp. 511-522; Published Jul. 12, 2016.

Fernandez, Javier et al.; "Healthy effects of prebiotics and their metabolites against intestinal diseases and colorectal cancer."; AIMS Microbiology 1(1), pp. 48-71; DOI: 10.3934/microbiol.2014.1.48; Published Nov. 23, 2015.

Machine-assisted translation of CN102366615A, obtained from https://worldwide.espacenet.com on Oct. 17, 2017; 11 pages.

International Search Report for International Application No. PCT/US2017/042329, dated Sep. 9, 2017; 7 pages.

Webpage for GI Effects® Comprehensive Profile-Stool, obtained from https://www.gdx.net/product/gi-effects-comprehensive-stool-test on Oct. 17, 2017; 5 pages.

Gibson, Glen R. et al.; "Dietary modulation of the human colonic microbiota: introducing the concept of prebiotics."; Journal of Nutrition 125(6), pp. 1401-12.; Published Jun. 1, 1995.

Eypasch, E. et al.; "Gastrointestinal Quality of Life Index: development, validation and application of a new instrument."; British Journal of Surgery 82(2), pp. 216-222; DOI:10.1002/bjs.1800820229; Published Feb. 1995.

Aspiroz, Fernando et al.; "Digestive Symptoms in Healthy People and Subjects With Irritable Bowel Syndrome: Validation of Symptom Frequency Questionnaire."; J Clin Gastroenterol 49(7), e64-70; DOI: 10.1097/MCG.0000000000000178; Published (online) Jul. 9, 2015.

Guyonnet, Denis et al.; "Fermented milk containing Bifidobacterium lactis DN-173 010 improves gastrointestinal well-being and digestive symptoms in women reporting minor digestive symptoms: a randomised, double-blind, parallel, controlled study." British Journal of Nutrition 102(11), pp. 1654-1662; DOI: 10.1017/S0007114509990882; Published (online) Jul. 22, 2009.

Guyatt, Gordon et al.; "A new measure of health status for clinical trials in inflammatory bowel disease."; Gastroenterology 96(2), pp. 804-810; Published Feb. 1989.

Hauser, Winfried et al.; "Development and validation of the Celiac Disease Questionnaire (CDQ), a disease-specific health-related quality of life measure for adult patients with celiac disease." Journal of Clinical Gastroenterology 41(2), pp. 157-166; DOI: 10.1097/01.mcg.0000225516.05666.4e; Published Feb. 2007.

Odamaki et al., "Age-related changes in gut microbiota composition from newborn to centenarian: a cross-sectional study", BMC Microbiol. May 25, 2016;16:90.

Avershina et al., "Transition from infant-to adult-like gut microbiota", Environ Microbiol. Jul. 2016;18(7):2226-36.

Meropol et al., "Development of the infant intestinal microbiome: A bird's eye view of a complex process", Birth Defects Res C Embryo Today. Dec. 2015;105(4):228-39.

Van Best et al., "On the origin of species: Factors shaping the establishment of infant's gut microbiota", Birth Defects Res C Embryo Today. Dec. 2015;105(4):240-51.

Segata, N., "Gut Microbiome: Westernization and the Disappearance of Intestinal Diversity", Curr Biol. Jul. 20, 2015;25(14):R611-3.

Bäckhed et al., "Dynamics and Stabilization of the Human Gut Microbiome during the First Year of Life", Cell Host Microbe. May 13, 2015;17(5):690-703.

Yatsunenko et al., "Human gut microbiome viewed across age and geography", Nature. May 9, 2012;486(7402):222-7.

* cited by examiner

COMPOSITIONS AND METHODS FOR MANAGING DIGESTIVE DISORDERS AND A HEALTHY MICROBIOME

CROSS-REFERENCE TO RELATED APPLICATIONS

This application claims priority to and all of advantages of U.S. Prov. Appl. No. 62/363,590 filed on 18 Jul. 2016, the contents of which is hereby incorporated by reference.

FIELD OF THE INVENTION

The present invention generally relates to a prebiotic composition and, more specifically, to a prebiotic composition comprising a combination of 2'fucosyllactose (2'FL) and isomaltooligosaccharide (IMO) and to related uses and methods associated with the prebiotic composition.

DESCRIPTION OF THE RELATED ART

Many animals, such as mammals, have a gastrointestinal (GI) tract that includes an epithelium, which typically functions as a selective barrier to permit the absorption of nutrients, electrolytes, and water, and that minimizes and/or prevent exposure of the bodies to dietary and microbial antigens. However, GI disorders have been shown to be associated with GI tracts having altered microbiota. In particular, dysbiosis (i.e., alteration of an intestinal microbiota) may result in neuroendocrine changes that contribute to pathogenesis of GI disorder(s). Animals, such as mammals (e.g. humans) afflicted by such GI disorder(s) may, as a result of the GI disorder(s), develop nutrient deficiencies and/or malnutrition.

Some of the GI disorders, such as irritable bowel syndrome (IBS), inflammatory bowel disease(s) (IBD), Crohn's disease, and ulcerative colitis (UC), which are each described in further detail below, affect a significant and growing number of humans in the United States (U.S.). One particular GI disorder is Celiac disease, which typically affects about 1% of the general population of the U.S. alone. Generally, these GI disorders have no cure, and current treatments often cause further complications in the afflicted host.

IBS is typically characterized by a combination of persistent and recurrent abdominal pain and irregular bowel habits such as diarrhea and/or constipation. Typical pharmacologic treatments (i.e., drug therapies) for IBS may include medications to manage abdominal pain, diarrhea, and constipation, and in certain instances, antibiotics. However, IBS has not been cured by such typical pharmacologic treatments.

IBD is typically characterized by chronic inflammation of all or part of a GI tract, and is often confused with IBS. Typically, IBD presents as ulcerative colitis or Crohn's disease, which each typically include diarrhea, pain, fatigue, and weight loss. IBD may be debilitating and, in certain instances, may lead to one or more life-threatening complications. Typical pharmacologic treatments for IBD include 5-aminosalicylates (e.g. 5-ASA), antibiotics, systemic and/or non-systemic glucocorticoids, immune-modulators, biologic therapies, anti-diarrheal medications, probiotics, and dietary interventions such the elimination of food triggers and (e.g. lactose avoidance).

Crohn's disease is an IBD that causes inflammation of tissues lining an affected GI tract. It is also understood that such inflammation may spread deep into the tissues of the affected GI tract, and may afflict different areas of the GI tract such as, for example large and/or small intestines. Crohn's disease is typically characterized by a combination of abdominal pain, diarrhea, vomiting, or weight loss, but may also include complications outside of the GI tract such as skin rashes, arthritis, and/or exhaustion. Like IBS, Crohn's disease has not been cured by typical pharmacologic treatments. Rather, treatments of Crohn's disease are typically restricted to controlling symptoms, maintaining remission, and preventing relapse.

UC (or Colitis ulcerosa) is a form of IBD, and is often considered similar to Crohn's disease. In particular, UC is an IBD characterized by long-lasting inflammation and sores (ulcers) in the innermost lining of the colon (i.e., large intestine, including the rectum) and, in some cases, the small intestine. As such, UC is a form of colitis (i.e., a disease of a colon), and includes a primary symptom of gradual onset bloody diarrhea. However, UC is an intermittent disease and includes both periods of exacerbated symptoms and also periods that are relatively symptom-free. Typical pharmacologic treatments for UC include anti-inflammatory drugs, immunosuppression, and biological therapies targeting specific immune responses. Other treatments for UC include surgical interventions such as colectomy (i.e., partial or total surgical removal of a colon) and total proctocolectomy (i.e., removal of the entirety of a colon and rectum). However, such surgical interventions may be associated with life-altering complications.

Celiac disease is an autoimmune disorder of the small intestine, and is characterized by symptoms including pain and discomfort in the GI tract, chronic constipation and/or diarrhea, failure to thrive (in children), and fatigue. In certain cases, vitamin deficiencies are often noted in people with celiac disease, and are typically thought to be caused by a reduction in an ability of the small intestine of an afflicted person to properly absorb nutrients from food. Treatments for celiac disease are typically limited to a life-long avoidance of dietary gluten. However, such treatments do not typically provide relief from symptoms.

SUMMARY OF THE INVENTION

A prebiotic composition comprising a combination of 2'fucosyllactose (2'FL) and isomaltooligosaccharide (IMO) is provided. The 2'FL and IMO can be present in the composition in a weight ratio of from 1:1 to 1:10.

In one embodiment, the prebiotic composition is included in a foodstuff or beverage. The foodstuff or beverage comprising the prebiotic composition can be suitable for use in methods of reducing or suppressing inflammation in an animalian gastrointestinal (GI) tract.

In another embodiment, the prebiotic composition is included in a kit presentation in combination with a pharmaceutical agent. The kit presentation can be suitable for use in methods of reducing or suppressing inflammation in an animalian GI tract.

In a further embodiment, the prebiotic composition is used in a method of preventing and/or treating a GI condition in an animal. The method can comprise administering the prebiotic composition to the animal.

DETAILED DESCRIPTION

Figure 1A:
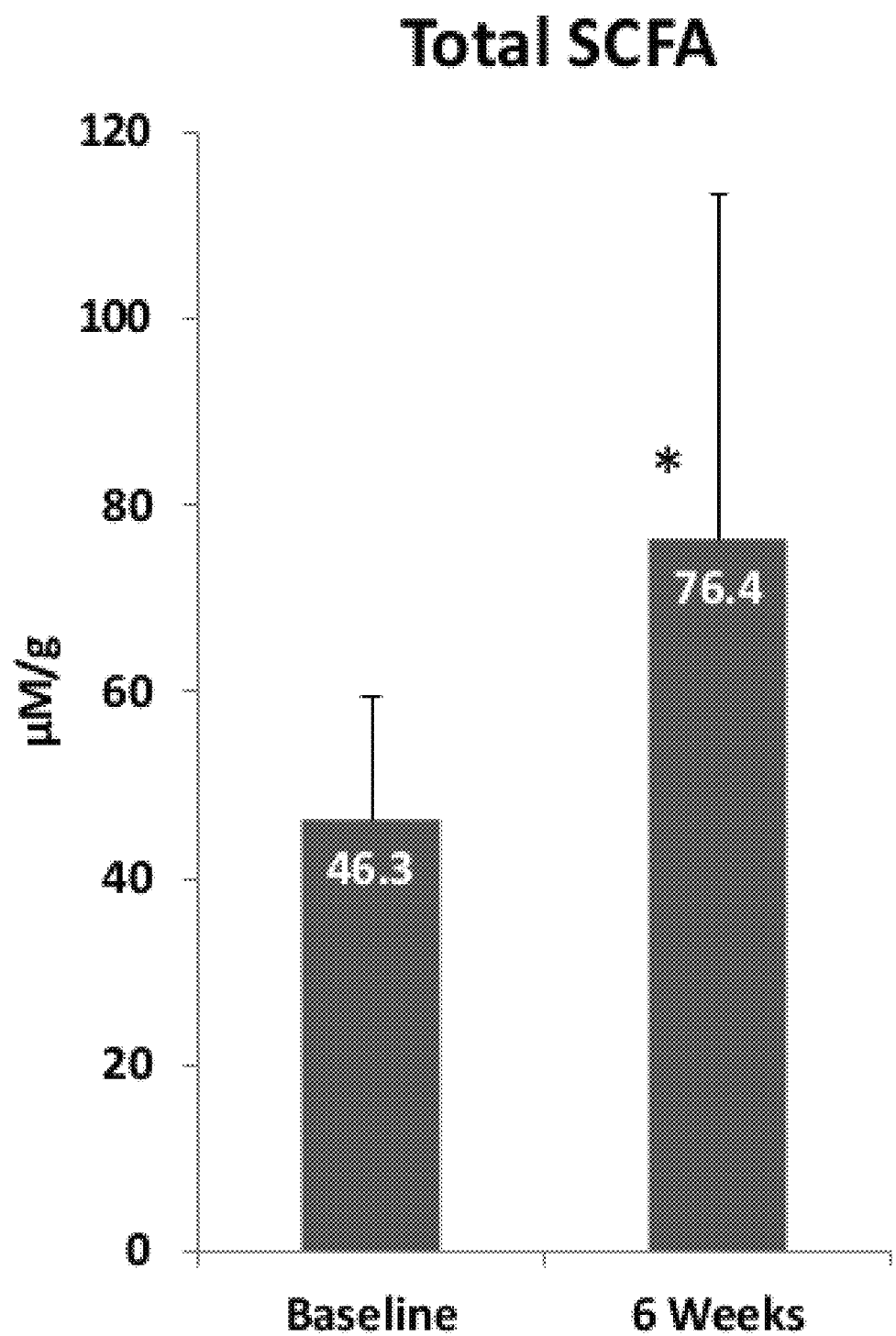
FIG. 1A is a bar chart illustrating enhanced production of total short chain fatty acids (SCFAs). The SOFA levels include the sum of butyrate, acetate, and propionate.

A prebiotic composition comprising a combination of 2'fucosyllactose (2'FL) and isomaltooligosaccharide (IMO), a foodstuff or beverage comprising the prebiotic composition, a kit presentation comprising the prebiotic composition, and a method of using the prebiotic composition are disclosed in greater detail below.

Definitions

As used herein, the singular forms "a", "an," and "the" are meant to include plural referents unless the context clearly dictates otherwise.

As used herein, an "embodiment" means that a particular feature, structure or characteristic is included in at least one or more manifestations, examples, or implementations of this invention. Furthermore, the particular features, structures or characteristics may be combined in any suitable manner, as would be apparent to a person skilled in the art. Combinations of features of different embodiments are all meant to be within the scope of the invention, without the need for explicitly describing every possible permutation by example. Thus, any of the claimed embodiments can be used in any combination.

As used herein, the term "weight percent" (and thus the associated abbreviation "wt. %") typically refers to a percent by weight expressed in terms of a weight of dry matter. As such, it is to be appreciated that a wt. % can be calculated on a basis of a total weight of a composition, or calculated from a ratio between two or more components/parts of a mixture (e.g. a total weight of dry matter).

As used herein, the terms "about" and "approximately", when referring to a specified, measurable value (such as a parameter, an amount, a temporal duration, and the like), is meant to encompass the specified value and variations of and from the specified value, such as variations of +/−10% or less, alternatively +/−5% or less, alternatively +/−1% or less, alternatively +/−0.1% or less of and from the specified value, insofar as such variations are appropriate to perform in the disclosed embodiments. Thus the value to which the modifier "about" or "approximately" refers is itself also specifically disclosed.

As used herein, the term "animal" refers to an organism of the kingdom Animalia that has a gastrointestinal (GI) tract. Examples of animals include mammals (i.e., vertebrates of the class Mammalia). All mammals have digestive tracts. Mammals that are specifically contemplated herein are domesticated mammals, such as dogs, cats, goats, sheep, pigs, cattle, horses, donkeys, camels, and the like. Additional mammals that are specifically contemplated herein include semi-domesticated mammals and mammals that are routinely bred in captivity. Of course, the term mammal also encompasses humans (which may be referred to as "people" and/or "person(s)." When describing a human, the term "adult" is typically used herein to refer to a human that has reached sexual maturity. By contrast, the terms "child" and "juvenile" are used herein to refer to a human that has not yet reached sexual maturity. Typically, the term "child" means a human subject between the stage of birth and the age of about 10 (i.e., childhood), and the term "juvenile" means a human subject that is greater than the age of about 10 and who has not completed the stage of puberty. Of course, the terms child, juvenile, adult, and infant are all encompassed by the term human, which is itself a subcategory of mammal, which is a subcategory of animal as defined herein.

As used herein, the term "gastrointestinal tract" (and thus the associated abbreviation "GI tract") refers to an organ system within an animal (e.g. a mammal) that ingests foodstuff, digests the foodstuff (e.g. to extract and/or absorb nutrients from the foodstuff or components thereof), and expels any non-digested component(s) of the foodstuff as waste (e.g. as urine and/or feces). In certain instances, the terms "digestive tract", "GIT", "gut", and "alimentary canal" may be used synonymously to refer to a GI tract. A GI tract may comprise multiple organs and/or anatomic structures, such as a mouth, esophagus, stomach, and intestine(s). Moreover, as will be understood by one of skill in the art, a GI tract may be divided into multiple systems, such as upper and lower tracts, and small and large intestines. Each of such systems may comprise a number of anatomic structures, including a buccal cavity, pharynx, esophagus, stomach, duodenum, jejunum, ileum, cecum, colon(s) (e.g. ascending, transverse, descending, and sigmoid colons, and colic flexure(s)), rectum, and anus.

As used herein, the term "prebiotic" refers to non-digestible food component which may selectively stimulate the growth and/or activity of one or a limited number of beneficial bacteria in a GI tract (e.g. in a colon) of a host (e.g. an animal) and thereby improve or maintain the health of the host. In particular instances, the term "prebiotic" may refer to a food comprising a non-digestible component that beneficially affects the host through selective metabolism in the host's GI tract. Without wishing to be bound by theory, it is thought that prebiotics may selectively stimulate the growth and/or activity of one or a limited number of bacteria in a part of the host's GI tract (e.g. a colon) and thereby improve the host's health.

As used herein, the term "prebiotic effect" refers to a selective, prebiotic-induced stimulation of growth and/or activity of one or a limited number of bacteria (e.g. bifidobacteria, lactobacilli, etc.) in the gut flora of a host that results in an improvement to the health of the host. Non-limiting examples of the improvements to the health of the host may include the alleviating constipation, improving gut health, improving mineral absorption, improving lipid metabolism, and/or improving satiety in the host.

The term "gut flora" refers to microorganisms (i.e., microflora) that normally live in the GI tract of an animal. For example, the gut flora present in a typical animal comprises pathogenic, benign, and beneficial microbial genera. The gut flora of a typical, healthy human comprises beneficial bacteria such as lactobacilli and bifidobacteria, and non-beneficial gut bacteria such as bacteroides, coliforms, clostridia, and sulfate-reducing bacteria. A predominance of such non-beneficial gut bacteria in the gut flora of an animal, such as a human, may lead to acute or chronic intestinal disorders including gastroenteritis, inflammatory bowel syndrome, irritable bowel syndrome, and intestinal cancer.

As used herein, the terms "treatment" and "treat" refer to and encompass prophylactic (i.e., preventive), modifying, and curative treatments. As such, these terms including treatment of patients (e.g. humans) at risk of contracting a disease or suspected to have contracted a disease, as well as patients who are ill or have been diagnosed as suffering from a disease or medical condition.

As used herein, the term "therapeutically effective amount" relates to an amount (i.e., a quantity) of a composition (e.g. the prebiotic composition of the present embodiments) required to achieve a particular therapeutic and/or prophylactic effect, such as in treating a patient. Likewise, as used herein, the term "physiologically effective amount" relates to an amount of a composition required to achieve a desired physiological effect. As will be understood by one of skill in the art, such effective amounts are typically measured and/or expressed in terms of g/day, or a derivative thereof (e.g. mg/day).

As used herein, the term "synergism" or "synergy" refers to an effect in which two or more agents (e.g. compounds) working together to produce a result not obtainable by any of the agents independently. As such, the term "synergistic amount" refers to amounts of the two or more agents at which a more pronounced (e.g. greater) effect is achieved as compared to the effects of each agent alone.

As used herein, the term "foodstuff" refers to a material that may be used as a food. As such, in certain instances the term foodstuff is used to describe a composition that may be consumed (e.g. by eating) by a living organism (e.g. a mammal), such as for nourishment and/or sustenance.

As used herein, the term "beverage" refers to a potable liquid or other non-solid composition. As such, in certain instances the term beverage is used to describe a non-solid (e.g. liquid, slurry, suspension, etc.) composition that may be consumed by a living organism for nourishment and/or sustenance. As such, in particular instances the terms "beverage" and "foodstuff" may overlap. In certain instances, the term "nutritional composition" is used to describe a foodstuff and/or beverage formulation that can be eaten or drunk by a human subject for nutrition.

As used herein, the term "functional food additive" refers to an ingredient, additive, component, or supplement suitable for incorporation in a foodstuff and/or beverage to confer a technical, nutritional, and/or health benefit (i.e., a function) to a host that consumes the foodstuff and/or beverage. Accordingly, such benefits may be closely related to a selective stimulation of some gut flora bacteria, and may include an alleviation of constipation, fan improved gut health, for an improved mineral absorption, an improved lipid metabolism, a better regulation of glycemia/insulinemia, and/or improved satiety (i.e., a prebiotic effect, as described above). The "functional food additive" can be added to different types of food including, but not limited to, medical foods, dietetic foods, and supplements.

As used herein, the term "medical food" is typically used to refer to a food for a special dietary use, such as a food formulated for dietary management of a medical condition (e.g. based upon scientific or medical evaluation). However, it is to be appreciated that the term "medical food" may have one or more particular definitions depending on, for example, geographic location, specific use, regulatory agency, and the like. For example, in certain cases, the term medical food may be defined as a food which is formulated to be consumed or administered enterally under the supervision of a physician and which is intended for the specific dietary management of a disease or condition for which distinctive nutritional requirements, based on recognized scientific principles, are established by medical evaluation (see, e.g., section 5(b) of the Orphan Drug Act (21 U.S.C. 360ee (b) (3)), which is incorporated herein by reference). In these or other instances, the term medical food may be defined as a food for special dietary use as a food that has been specially processed or formulated to meet the particular requirements of a person: (a) in whom a physical or physiological condition exists as a result of a disease, disorder, or injury; or (b) for whom a particular effect, including but not limited to weight loss, is to be obtained by a controlled intake of food (see, e.g., section 8.24.001 of the Canadian Food and Drug Regulations (FDR, C.R.C., c. 870)(as amended 13 Jun. 2017)), which is incorporated herein by reference).

As used herein, the term "supplement" relates to a nutritional supplement which is a concentrated source of nutrient or alternatively other substances with a nutritional or physiological effect whose purpose is to supplement the normal diet.

As used herein, the term "carbohydrate" refers to a polyhydroxy-aldehyde (aldose) or ketone (ketose) compound (i.e., typically referred to as saccharides or sugars), or to a substance which yields one or more of such compounds upon hydrolysis. Examples of carbohydrates include mono-, poly-, and oligosaccharides, as well as certain fermentable carbohydrates. Polysaccharides are carbohydrates composed of a many monosaccharides (e.g. 20 or more) that are linked via glycosidic linkages. Non-limiting examples of naturally occurring polysaccharides are plant cell wall polysaccharides such as cellulose, pectins, arabinans/arabans, arabinoxylans, xylans, arabinogalactans, xyloglucans, and beta-glucans, or other polysaccharides such as starches, galactomannans, mannans, arabinogalactans, and fructans. Oligosaccharides are carbohydrates composed of a limited number of monosaccharides (e.g. fewer than 20) that are linked by glycosidic linkages. Non-limiting examples of naturally occurring oligosaccharides are saccharose, cellobiose, raffinose, xylo-oligosaccharides, fructo-oligosaccharides, and galacto-oligosaccharides.

As used herein, the term "fermentable carbohydrates" refers to oligosaccharides and/or polysaccharides that are not generally digestible or useful to an animal (e.g. a mammal), but may be fermentable by gut flora present in the animal. For example, in certain instances, fermentable carbohydrates comprise oligosaccharides and/or polysaccharides that escape digestion and/or absorption in an upper digestive tract of a mammal (e.g. a human), and are subsequently fermented by endogenous microflora (i.e., the gut flora) in a large intestine of the mammal. Such a fermentation process may generate gas(es) and/or short-chain fatty acids. Included in this definition are the IMO and 2'FL oligosaccharides of the oligosaccharide prebiotic composition described herein.

As used herein, the term "peptide" describes a molecule having 2 or more amino acids joined together by a peptide bond. As will be understood by those of skill in the art, the term "peptide" encompasses oligopeptides (i.e., peptides comprising 20 or fewer, alternatively 10 or fewer amino acids, e.g. di-, tri-, tetra-, and pentapeptides, etc.) polypeptides (i.e., peptides comprising greater than 10, alternatively greater than 20 amino acids), proteins (i.e., organic compounds comprising amino acids linked via peptide bonds in a linear chain and folded into a globular form), enzymes (i.e., functional proteins), and the like. Such peptides may include any known amino acid, such as the 20 gene-encoded amino acids or others such as selenocysteine. Additionally, the term "peptide" also encompasses naturally modified peptides, e.g. peptides naturally and/or synthetically modified by glycosylation, acetylation, phosphorylation, and the like, or any combination thereof. Furthermore, the term "peptide" also encompasses branched peptides, especially those known to have therapeutic or beneficial effects. It is to be appreciated that the peptides described herein may be produced recombinantly, synthetically, or semi-synthetically, or obtained from natural sources (e.g. via isolation after hydrolysis of a protein and/or enzyme).

As used herein, the term "lipid" refers to naturally occurring and/or synthetic small molecules that exhibit hydrophobic or amphiphilic properties and typically form vesicles, multilamellar/unilamellar liposomes, and/or membranes in an aqueous environment. As will be understood by one of skill in the art, the term "lipid" encompasses oils, fats (e.g. triclygerides), fatty acids, waxes, sterols, fat-soluble vitamins (e.g. vitamin A, D, E, K, etc.), glycerolipids (e.g. monoglycerides, diglycerides, triglycerides, glycerols, etc.), phospholipids, Sphingolipids, sterols, prenols, saccarolipids, and the like.

As used herein, the term "short chain fatty acids" (and thus the associated abbreviation "SOFA") refers a sub-group of fatty acids with aliphatic chains containing less than six carbons in a backbone. They include, but are not limited to, acetic acid, propionic acid, isobutyric acid, butyric acid, isovaleric acid, valeric acid, caproic acid, lactic acid, and succinic acid.

The Prebiotic Composition

As introduced above, in one aspect, the present embodiment includes a prebiotic composition. More specifically, the prebiotic composition comprises a synergistic combination 2'fucosyllactose (2'FL) and isomaltooligosaccharide (IMO). Moreover, the prebiotic composition is suitable for use in a method of preventing and/or treating a GI condition in an animal, as described in further detail below.

For clarity, it is to be understood that the compound name "2'fucosyllactose" (and thus the associated abbreviation "2'FL") is used herein to describe a chemical compound having a chemical formula of $C_{18}H_{32}O_{15}$, an associated CAS number of 41263-94-9, and the following chemical structure:

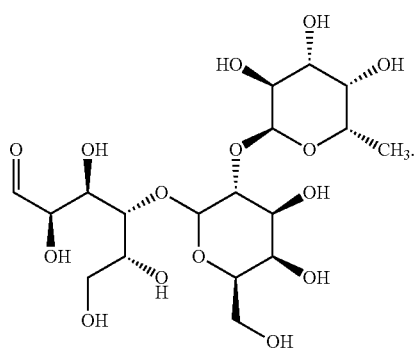 [SMILES: C[C@@H]1O[C@@H](O[C@H]2C(O[C@@H]([C@H](O)[C@@H](O)C=O)[C@H](O)CO)O[C@H](CO)[C@H](O)[C@@H]2O)[C@@H](O)[C@H](O)[C@@H]1O]

The prebiotic composition may comprise 2'FL from any source, such as naturally-occurring 2'FL (e.g. from milk, including human breast milk), and/or synthetic 2'FL (e.g. synthesized or expressed via recombinant DNA technology). In certain embodiments, the 2'FL may be synthesized and/or derived from a naturally occurring precursor (e.g. lactose).

Without wishing to be bound by theory, it is believed that 2'FL provides the inventive prebiotic composition with abilities to support the growth of beneficial microbiota (e.g. *Bifidobacterium*), regulate gut motility (by reducing the frequency and velocity of contractions), and induce production of certain SCFAs via GI fermentation. These certain SCFAs are believed to decrease intra-luminal pH, directly inhibit the growth and/or activity of harmful microorganisms, and encourage the growth of beneficial bacteria (e.g. *Bifidobacterium*) that compete with potentially pathogenic microorganisms for nutrients and epithelial adhesion sites in mammalian GI tracts.

The prebiotic composition may comprise any amount of 2'FL, such as from 2 to 8, alternatively from 3 to 7, alternatively from 4 to 6, alternatively from 4.5 to 5.5, weight percent (wt. %) of 2'FL, based on the total weight of the prebiotic composition. In certain embodiments, the prebiotic composition comprises 2, 2.5, 3, 3.5, 4, 4.5, 5, 5.5, 6, 6.5, 7, 7.5, or 8, wt. % 2'FL, based on the total weight of the prebiotic composition. In particular embodiments, the prebiotic composition comprises 5 wt. % 2'FL, based on the total weight of the prebiotic composition.

It is to be appreciated that the particular amount of 2'FL present in the prebiotic composition may vary in accordance with the total weight of the prebiotic composition, which may be measured and/or described on the bases of a sample, a serving size, a batch, or an average of one or more samples, serving sizes, or batches. Typically, the amount of 2'FL present in the prebiotic composition is measured and/or described with reference to a serving size of the prebiotic composition as described herein. For instance, in a 40 g serving size of the prebiotic composition, the 2'FL is typically present in an amount of from 0.75 to 3.25 g, such as from 1 to 3, alternatively from 1.25 to 2.75, alternatively from 1.5 to 2.5, alternatively from 1.75 to 2.25, alternatively of 2, g.

For clarity, it is to be understood that the compound name "isomaltooligosaccharide" (and thus the associated abbreviation "IMO") is used herein to describe a chemical composition characterized by inclusion of a mixture of short-chain carbohydrates, such as glucose oligomers including isomaltose, panose, isomaltotriose, isomaltotetrose, isomaltopentose, isomaltohexose, and isomaltoheptose. As such, IMO is a branched oligosaccharide containing a series of α-(1,6) bonds in its structure. Typically, IMO includes oligosaccharide polymers comprising 4-7 repeating monomeric units of isomaltose (i.e., 6-O-α-D-glucopyranosyl-D-glucose, CAS no. 499-40-1), which can be represented by the following chemical formula:

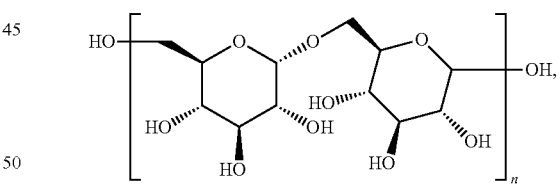

where n is 4, 5, 6, or 7.

The prebiotic composition may comprise IMO from any source, such as naturally-occurring IMO (e.g. from honey) and/or synthetic IMO (e.g. as produced via enzymatic conversion of starch). In certain embodiments, the IMO may be synthesized and/or derived from a naturally occurring precursor (e.g. starch from cereal crops like wheat, barley, potato, and the like).

Without wishing to be bound by theory, it is believed that IMO is a prebiotic soluble fiber which supports the production of certain SOFA end products via GI fermentation. These certain SCFAs are believed to decrease intra-luminal pH, directly inhibit the growth and/or activity of harmful microorganisms, and encourage the growth of beneficial bacteria (e.g. *Bifidobacterium*) that compete with potentially pathogenic microorganisms for nutrients and epithelial adhesion sites in mammalian GI tracts.

As introduced above, the prebiotic composition comprises a synergistic combination of the 2'FL and the IMO. Typically, the synergistic combination comprises the 2'FL and the IMO in a weight ratio (w/w) of 2'FL:IMO of from 1:1 to 1:10, alternatively of from 1:2 to 1:5, alternatively of 1:2.5. As the prebiotic composition comprises the synergistic combination of the 2'FL and the IMO, the 2'FL and the IMO may likewise be present in the prebiotic composition itself in a weight ratio of 2'FL:IMO of from 1:1 to 1:10. In certain embodiments, the 2'FL and the IMO are present in the prebiotic composition in a weight ratio of 2'FL:IMO of from 1:2 to 1:5. In some embodiments, the 2'FL and the IMO are present in the prebiotic composition in a weight ratio of 2'FL:IMO of 1:2.5.

It is to be understood that the prebiotic composition may comprise any amount of IMO, so long as the synergistic combination of the 2'FL and the IMO present in the prebiotic composition comprises the 2'FL and the IMO in weight ratio (w/w) of 2'FL:IMO within the ranges described herein. For example, the prebiotic composition may comprise from 2 to 80, alternatively from 2 to 72, alternatively from 4 to 64, alternatively from 4 to 56, alternatively from 6 to 48, alternatively from 6 to 40, alternatively from 8 to 32, alternatively from 8 to 24, alternatively from 10 to 16, alternatively from 12 to 13, weight percent (wt. %) of IMO, based on the total weight of the prebiotic composition. In certain embodiments, the prebiotic composition comprises 2, 4, 5, 6, 8, 9, 10, 11, 11.5, 12, 12.5, 13, 13.5, 14, 15, 16, 20, 24, 25, 30, 32, 35, 40, 45, 48, 50, 56, or 72, wt. % IMO, based on the total weight of the prebiotic composition. In particular embodiments, the prebiotic composition comprises 12.5 wt. % IMO, based on the total weight of the prebiotic composition.

It is to be appreciated that the particular amount of IMO present in the prebiotic composition may vary in accordance with the total weight of the prebiotic composition, which may be measured and/or described on the bases of a sample, a serving size, a batch, or an average of one or more samples, serving sizes, or batches. Typically, the amount of IMO present in the prebiotic composition is measured and/or described with reference to a serving size of the prebiotic composition as described herein. For instance, in a 40 g serving size of the prebiotic composition, the IMO is typically present in an amount of from 0.75 to 32.5 g, such as from 0.75 to 29.25, alternatively from 1 to 26, alternatively from 1.5 to 22.75, alternatively from 1.5 to 19.5, alternatively from 2 to 19.5, alternatively from 2.25 to 16.25, alternatively from 3 to 13, alternatively from 3.75 to 10, alternatively from 4 to 9.75, alternatively from 4 to 8, alternatively from 4.5 to 6.5, alternatively from 4.5 to 6, alternatively of 5, g.

The prebiotic composition may include one or more additional components. Examples of suitable additional components include fat and/or lipid components, protein components, and additive components.

In certain embodiments, the prebiotic composition includes a fat and/or lipid component. The fat and/or lipid component comprises fats (e.g. saturated, monounsaturated, polyunsaturated, and/or unsaturated) and/or lipids (e.g. cholesterol, other sterols). In certain embodiments, the fat and/or lipid component comprises sunflower oil, flaxseed oil, medium chain triglycerides, or a combination thereof. The prebiotic composition may comprise the fat and/or lipid component in any suitable amount. In particular embodiments, the prebiotic composition includes the fat and/or lipid component in an amount of from 12.5 to 30 wt. %, based on the total weight of the prebiotic composition. In certain embodiments, the prebiotic composition comprises 17.5 wt. % of the fat and/or lipid component.

In some embodiments, the prebiotic composition includes a protein component. The protein component typically includes a protein source, such as individual amino acids, peptides, oligopeptides, and/or proteins. In certain embodiments, the protein component comprises pea protein isolate and/or rice protein concentrate. In these or other embodiments, the protein component comprises L-alanyl-L-glutamine, L-alanine, L-arginine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-Valine, selenomethionine, or a combination thereof.

In particular embodiments, the prebiotic composition includes the protein component in an amount of from 25 to 75, alternatively from 35 to 50, alternatively of 45, wt. %, based on the total weight of the prebiotic composition. In certain embodiments, the prebiotic composition comprises 45 wt. % of the protein component.

In particular embodiments, the prebiotic composition includes an additive component comprising one or more additive suitable for use in a prebiotic composition. The additive component may comprise the fat and/or lipid component and/or the protein component, as each described above. Alternatively, the additive component may be separate from the fat and/or lipid component and/or the protein component, if present within the prebiotic composition. As such, it is to be appreciated that prebiotic composition may comprise one or more of the fat and/or lipid component, the protein component, and the additive component. In embodiments where each of such components is present in the prebiotic composition, the additive component may comprise an amino acid, a peptide, and/or a protein that is the same as or different than any one or more amino acid, peptide, and/or protein present in the protein component. Likewise, the additive component may comprise a fat and/or lipid that is the same as or different than any fat and/or lipid present in the fat and/or lipid component. As such, the ranges listed herein with respect to the any particular component may encompass the total amount of such component (e.g. the protein, lipid, and/or additive components) present within the prebiotic composition, or may refer merely to amount of a single, particular component described therewith.

Examples of suitable additives for use in the additive component include amino acids, peptides, proteins, lipids, vitamins, carbohydrates, nucleic acids, minerals, anabolic nutrients, antioxidants, probiotic bacterial strains, lipotropic agents, extracts, concentrates, oils, gums, and combinations thereof. In certain embodiments, the prebiotic composition comprises the additive component, and the additive component comprises an amino acid, a peptide, a protein, a lipid, a vitamin, a carbohydrate, a nucleic acid, a mineral, an anabolic nutrient, an antioxidant, a probiotic bacterial strain, a lipotropic agent, or any combination thereof. In these or other embodiments, the additive component comprises a flavoring agent, a dye, a flow modifier, a preservative, a filler, a binder, a dispersing agent, a carrier, a supplemental nutrient, or any combination thereof. In particular embodiments, the additive component comprises a carrier, such as a consumable, nutritional, and/or pharmaceutical carrier, or a combination thereof.

In addition to those additives listed above, specific examples of additives suitable for use in the additive component include pea protein isolate, isomalto-oligosaccharide, rice protein concentrate, 2'-fucosyllactose powder, flaxseed, organic cane sugar, natural flavors, high oleic sunflower oil, L-lysine HCl, medium chain triglycerides, L-leucine, Silica, L-valine, L-alanyl-L-glutamine, L-isoleucine, xanthan gum, vitamins, minerals, zinc gluconate, ascorbic acid, manganese gluconate, alpha tocopheryl acetate, copper gluconate, D-biotin, retinyl palmitate, niacinamide, cholecalciferol, calcium pantothenate, chromium picolinate, pyridoxine HCl, riboflavin, potassium iodide, thiamin HCl, calcium L-5-methyltetrahydrofolate, selenomethionine, and methylcobalamin, Luo Han Guo fruit (monk fruit) extract, vanilla, rosemary extract, cocoa powder, vitamin E, thiamin, riboflavin, niacin, vitamin B6, folate, vitamin B12, biotin, pantothenic acid, phosphorus, iodine, magnesium, zinc, selenium, copper, manganese, and the like, and combinations thereof.

In particular embodiments, the prebiotic composition includes the additive component in an amount of from 12.5 to 75, alternatively from 17.5 to 75, alternatively from 17.5 to 50, alternatively from 25 to 50, alternatively from 25 to 45, alternatively from 35 to 50, alternatively from 35 to 45, alternatively of 17.5, 25, 35, 45, or 50 wt. %, based on the total weight of the prebiotic composition.

In some embodiments, the prebiotic composition includes at least one additive comprising an amino acid, a peptide, and/or a protein, and the at least one additive is present in an amount of from 10 to 30 grams, alternatively from 15 to 20 grams, alternatively of 18 grams, per 40 gram dry weight sample of the prebiotic composition.

In certain embodiments, the prebiotic composition includes at least one additive comprising a lipid, and the lipid is present in an amount of from 5 to 12 grams, alternatively of 7 grams, per 40 gram dry weight sample of the prebiotic composition.

The prebiotic composition may compose any form, such as a dry powder, a solution, a suspension, an emulsion, or the like. In certain embodiments, the prebiotic composition is a dry powder. In some embodiments, the prebiotic composition is adapted to be consumed as a liquid. For example, the prebiotic composition may be a dry powder that is combined with a consumable liquid (e.g. water) to form a consumable liquid solution, suspension, or emulsion comprising the prebiotic composition. Likewise, the prebiotic composition may be adapted to be mixed with a foodstuff or beverage. As such, in some embodiments, the prebiotic composition is, alternatively is a component of, a foodstuff or beverage. In these or other embodiments, the prebiotic composition may be further defined as a food additive. Accordingly, it is to be appreciated that certain aspects of the present embodiments include the use of the prebiotic composition as a food additive, and the use of the prebiotic composition in methods of preparing foodstuff and/or beverages.

As introduced above, the present embodiments can include a foodstuff or beverage comprising the prebiotic composition. The foodstuff or beverage is typically suitable for use in methods of reducing or suppressing inflammation in an animalian GI tract or a cause or symptoms thereof, such as diarrhea, inflammatory bowel disease (IBD), Crohn's disease, enterocolitis, ulcerative colitis, allergic colitis, irritable bowel syndrome, pouchitis, post-infection colitis, *Clostridium difficile*-associated diarrhea, Rotavirus-associated diarrhea, post-infective diarrhea, and/or diarrheal disease due to an infectious agent (e.g. *E. coli*), IBS, Celiac disease, intolerances, allergies, and combinations thereof.

Typically, the foodstuff or beverage comprises an admixture of the prebiotic composition with one or more feed products, liquids, supplements, or combinations thereof. In particular embodiments, the foodstuff or beverage comprises 40 g of the prebiotic composition per serving/unit dose of the foodstuff or beverage. However, in certain embodiments the prebiotic composition may itself be further defined as a foodstuff or beverage composition, depending on the quantity, nature, and identity of individual additives and components present in the prebiotic composition, such as those described above. Thus, it is to be appreciated that the embodiments described herein with respect to the prebiotic composition are intended to equally encompass the foodstuff or beverage, a food or beverage product, and/or a food supplement comprising the prebiotic composition. For example, in certain embodiments, the foodstuff or beverage comprising the prebiotic composition comprises a fat and/or lipid component, a protein component, an additive component, or a combination thereof. As such, it is to be appreciated that any amount of fat and/or lipids, protein (e.g. amino acids, peptides, protein, etc.), and additives present in the prebiotic composition will thus also be present in the foodstuff or beverage comprising the prebiotic composition. Accordingly, any amounts and/or examples of such components described herein with respect to the prebiotic composition itself may equally apply to the foodstuff or beverage comprising the prebiotic composition, as will be understood by one of skill in the art.

Typically, the foodstuff or beverage comprising the prebiotic composition comprises from 5 to 12 grams of fat components, if any, from 5 to 12 grams of lipid components, if any, and from 10 to 30 grams of protein components, if any, each based on a 40 gram dry weight sample of the foodstuff or beverage.

In some embodiments, the foodstuff or beverage comprising the prebiotic composition is further defined as a nutritional composition. The nutritional composition typically has a nutritional value of at least 1 kilocalorie (kcal) per 100 grams (g) for dry food formulations (i.e., foodstuffs), or per 100 milliliters (ml) for liquid formulations (i.e., beverages). In certain embodiments, the nutritional composition has a nutritional value of at least 10, alternatively at least 50, alternatively at least 100, alternatively at least 300, kcal per 100 g for dry food formulations (i.e., foodstuffs), or per 100 ml for liquid formulations (i.e., beverages). In at least one embodiment, the nutritional formulation has a nutritional value of from 50 to 200 kcal/100 ml for liquid formulations, and of from 300 to 600 kcal/100 g for dry food formulations. In these or other embodiments, the nutritional composition is in the form of a dry food concentrate, which may be mixed with liquid or food and subsequently consumed. It is to be appreciated that the nutritional composition is distinguished from a vaccine, and the compositions described herein may be free, alternatively substantially free, from a vaccine.

In addition to the components described above with respect to the prebiotic composition and the foodstuff or beverage comprising the prebiotic composition, the nutritional composition may further comprise ingredients selected from lipids, minerals, carbohydrates, amino acids, amino acid chelates, anabolic nutrients, vitamins, antioxidants, probiotic bacterial strain, lipotropic agents, and the like, which may each be independently selected in order to provide the nutritional composition with a formulation capable of sustaining energy and/or anabolism in an animal.

In certain embodiments, the nutritional composition may be further defined as a nutritional supplement, or as a complete nutritive. For example, the nutritional composition may be formulated to provide a mammal (e.g. a human), via consumption of the nutritional composition, with at least 5%, alternatively at least 10%, alternatively at least 25%, alternatively at least 50%, alternatively at least 75%, alternatively at least 90%, of daily calories required by the mammal. However, it is to be appreciated that a daily calorie requirement is dependent on several factors, including the gender, height, and/or age of the mammal, and thus the percentage of caloric requirement provided by the nutritional composition will be dependent on the particular person consuming the nutritional composition. For example, a 30 year old human male of 80 kg body weight and 180 cm height has a daily calorie requirement of around 2900 cal (calories) to maintain his body weight whereas a 30 year old human female of 55 kg body weight and 165 cm height has a daily calorie requirement of around 2100 cal to maintain her body weight. In at least one embodiment, the nutritional formulation is a nutritional product for human infants or juveniles.

In certain embodiments, the foodstuff or beverage is further defined as an animal food. In such embodiments, the foodstuff or beverage is typically formulated for ingestion by one or more non-human animals, such as livestock including cattle, swine, horses, sheep, goats, poultry, and fish, domesticated companionship species such as dogs, cats, fish, and rodents, undomesticated wildlife such as deer, moose, elk, migratory, and non-migratory fowl, those non-human animals described herein, and combinations thereof.

In some embodiments, the foodstuff or beverage is further defined as a medical food. As such, it is to be appreciated that the medical food comprises the prebiotic composition, and may be the same as or different from the nutritional composition described above.

In certain embodiments, the prebiotic composition and the medical food are formulated such that a 40 g dry weight serving of the medical food contains the lipid component in an amount of from 5 to 12 g, alternatively of 7 g. In these or other embodiments, the medical food is formulated such that a 40 g dry weight serving of the medical food contains the protein component in an amount of from 10 to 30 g, alternatively of from 15 to 20 g, alternatively of 18 g.

As introduced above, the present embodiments can provide a kit presentation, comprising a combination of the prebiotic composition a pharmaceutical agent, for use in a method of reducing or suppressing inflammation in an animalian GI tract.

The kit presentation comprising the prebiotic composition the pharmaceutical agent may be configured, and thus used, for providing separate, sequential, or simultaneous administration of the prebiotic composition and the pharmaceutical agent, or a treatment comprising the pharmaceutical agent. Accordingly, the prebiotic composition and the pharmaceutical agent may be formulated together in standard pharmaceutical dosage forms known in the art.

The pharmaceutical agent may be any pharmaceutical agent suitable for use in combination with the prebiotic composition. Typically, the pharmaceutical agent comprises mesalamine, sulphasalazine, a 5-ASA agent, a corticosteroid (e.g. adrenal steroids, prednisone, hydrocortisone, budesonide, etc.), an anti-inflammatory medication, an antibody therapeutic agent (e.g. ENTYVIO®), a drug used against pain, diarrhea, and/or infection, a serotonin-4 receptor agonist (e.g. ZELNORM®/ZELMAC®), or a combination thereof. It is to be appreciated that combining the prebiotic composition with a treatment or therapy comprising the pharmaceutical agent is expressly contemplated herein. As such, reference to the pharmaceutical agent is to be understood to encompass treatments and therapies which include the pharmaceutical agent, and not merely the pharmaceutical agent itself.

In addition to the pharmaceutical therapies described herein, the prebiotic composition may also be used in combination with supplements commonly used by patients suffering from GI conditions, non-limiting examples of which include multivitamins, fish oils and omega fatty acids (e.g. EPA, DHA, etc.), probiotics, and/or certain medical foods (e.g., ENTERAGAM®, PODIAPN™, ULTRAINFLAMX®, and the like). Accordingly, the kit presentation may comprise such a supplement in addition to the pharmaceutical agent.

As introduced above, a further embodiment includes the use of the prebiotic composition in a method of preventing and/or treating a GI condition in an animal. In particular, the prebiotic composition described herein has surprisingly been found to be useful in a method of, or as a therapeutic for, preventing, treating, and/or reducing GI (e.g. intestinal) inflammation associated with GI conditions.

Accordingly, in some embodiments, the prebiotic composition is useful in a method of preventing and/or treating a GI condition in an animal (e.g., a mammal, a human). In these or other embodiments, the prebiotic composition is useful in a method of prophylactically treating a GI condition. More specifically, in certain embodiments, the prebiotic compositions described herein is administered to treat an individual suffering from any of a number of diseases or medical conditions characterized by or associated with GI inflammation, such as IBS, IBD, UC, Crohn's disease, diarrhea, constipation, diabetes, hypertension, dyslipidemia, obesity, heart disease, stroke, and those other conditions described above, or a combination thereof. In these or other embodiments, the prebiotic composition is administered to treat (e.g. prophylactically) an individual who has undergone surgical intervention (e.g. removal of all or part of the individual's GI tract, such as an ileocecal valve, etc.).

Typically, the method of preventing and/or treating the GI condition in the animal comprises administering the prebiotic composition to the animal (i.e., using the prebiotic composition) to prevent, reduce, or eliminate symptoms and/or causes of one or more GI conditions. For example, in particular embodiments the prebiotic composition is used to prevent and/or treat IBS, IBD, Celiac disease, Ulcerative colitis, Crohn's disease, or a combination thereof. However, in certain embodiments, preventing and/or treating the GI condition comprises healing or restoring health to a GI tract of the animal, reducing or suppressing inflammation in the GI tract of the animal, restoring a GI function in the animal, reducing an amount of a pathogen present in a large intestine of the animal, improving or enhancing a quality of life of the animal, or a combination thereof. As such, in certain embodiments, the method of preventing and/or treating the GI condition in the animal using the prebiotic composition may be further defined as a synergistic method of healing, assisting in the health of, restoring the health of, or an adjunct therapy for, the GI condition.

In particular embodiments, preventing and/or treating the GI condition comprises improving or enhancing the quality of life of the animal. In some such embodiments, the animal is a human and the method of preventing and/or treating the GI condition comprises improving or enhancing the quality of life of the human on a basis of a validated quality of life questionnaire, such as the Digestive Symptom Frequency Questionnaire (DSFQ), the Gastrointestinal Quality of Life Index (GIQLI), and/or the Inflammatory Bowel Disease Questionnaire (IBDQ), regardless of which GI condition is present.

It is to be appreciated that the prebiotic composition may be administered to the animal by any means known in the art, including via topical, enteral, or parenteral routes. Typically, the prebiotic composition is administered orally. However, rectal and/or enteral administration may also be used.

The method of using the prebiotic composition described above may further include shifting a gut microbiome of a host (e.g. an animal, mammal, human, etc.) to a more optimal profile. Such a shift may include and/or result in a decrease in a number of potential pathogens and/or an increase the presence of beneficial butyrate-producing microbe (i.e., improve the host's gut profile). An improved gut profile may provide the host with a decreased risk of digestive irregularities that can lead to one or more digestive disorders, which can progress to more advanced conditions such as IBS, IBD, and other compromised health states including those described above. As such, in accordance with the method of using the prebiotic composition described above, the prebiotic composition may be administered to a host to promote the growth of beneficial bacteria in the host's GI tract and thereby prevent or reduce a likelihood of the host suffering from a disease or GI condition, such as one of those described above. For example, *Roseburia hominis* and *Faecalibacterium prausnitzii* are butyrate-producing species known to be deficient in patients with IBD, and both species display an inverse correlation with UC disease activity. Additionally, an increased presence of *Bifidobacterium* spp. In a GI tract of a mammal is a known indicator of GI health. Accordingly, in some embodiments, the method of using the prebiotic composition further comprises increasing a level (e.g. growth, number, etc.) of *Bifidobacterium* spp., *Faecalibacterium prausnitzii*, and/or *Roseburia* spp. in the GI tract of the host. Without wishing to be bound by theory, it is believed that butyrate producing bacteria are generally beneficial to a host and may improve intestinal barrier function and reduce methane-producing microorganisms in the host's colon, which in turn will thereby reduce abdominal gas in the host. In these or other embodiments, the prebiotic composition is administered to the host to reduce the growth and/or number of pathogens in the host's GI tract (e.g. the host's large intestine)

In certain embodiments, the method of preventing and/or treating the GI condition in the host further comprises increasing or stabilizing a level of butyrate in a large intestine of the host. In such embodiments, the method may further comprise normalizing a butyrate level in the gut to support healthy colonocytes in the GI tract of the host. In these or other embodiments, the method of preventing and/or treating the GI condition in the host further comprises increasing a level of short chain fatty acids (SCFAs) in a large intestine of the host.

A further embodiment includes the use of the prebiotic composition in a method of providing nutritional support in combination with a therapy to a host afflicted by a GI condition. The method includes administering the therapy and administering the prebiotic composition as described above. The therapy may be any therapy and/or treatment for the GI condition. The prebiotic composition may be administered to the host as a stand-alone composition, or as one or more of the foodstuff, beverage, nutritional composition, medical food, and kit presentation described above. In certain embodiments, the method of providing nutritional support in combination with the therapy further comprises administering a vitamin and/or mineral supplement to the host.

In certain instances, administering the prebiotic composition to a host in accordance with the method described above may result in an increased yield in one or more host-derived commodity, such as eggs, meat, milk, wool, or combinations thereof.

The prebiotic composition may be administered as needed, daily, several times per day or in any suitable regimen such that the desired outcome is achieved. In the methods, the frequency of administration can depend on several factors, including the desired level of prevention and/or treatment. Generally, a regimen includes administration of the prebiotic composition to the host once or twice daily to include an administration in the morning and/or an administration in the evening. The amount of prebiotic composition administered to the host during each administration may depend on several factors including level of desired results and the specific prebiotic composition.

Additional Embodiments

The following additional embodiments are provided, the numbering of which is not to be construed as designating levels of importance. Moreover, it is to be understood that the embodiments recited below are provided in conjunction with and in addition to the embodiments described above, as well as those claimed further below. Thus, it is also to be understood that variations, combinations, and/or modifications of the embodiment(s) and/or features of the embodiment(s) may be within the scope of the present invention. Likewise, alternative embodiments that result from combining, integrating, and/or omitting features of the embodiment(s) described herein may also be within the scope of the present invention.

Embodiment 1 relates to a composition comprising a combination of 2'fucosyllactose (2'FL) and isomaltooligosaccharide (IMO) in a ratio of about 1:1 to about 1:10, capable of reducing or suppressing inflammation in an animalian gastrointestinal (GI) tract.

Embodiment 2 relates to the composition of embodiment 1, wherein the synergistic combination is in a ratio of about 1:2 to about 1:5.

Embodiment 3 relates to the composition of embodiment 1, wherein the synergistic combination is in a ratio of about 1:2.5.

Embodiment 4 relates to the composition of any one of the preceding embodiments, wherein the composition is formulated into a medical food.

Embodiment 5 relates to the composition according to any one of the preceding embodiments, wherein the composition is adapted to be consumed as a liquid.

Embodiment 6 relates to the composition according to any one of the preceding embodiments, wherein the composition is provided as a dry powder.

Embodiment 7 relates to the composition according to any one of the preceding embodiments, wherein the composition is provided as a dry powder, and wherein the dry powder is adapted to be dissolved in at least one of water and a consumable liquid.

Embodiment 8 relates to the composition according to any one of the preceding embodiments, wherein the composition is provided in a form adapted to be mixed with a foodstuff.

Embodiment 9 relates to the composition according to any one of the preceding embodiments, wherein the composition further comprises a vitamin.

Embodiment 10 relates to the composition according to any one of the preceding embodiments, wherein the composition further comprises at least one of an amino acid, a peptide, and a protein.

Embodiment 11 relates to the composition according to embodiment 10, wherein the at least one of the amino acid, the peptide, and the protein is present in amount of about 10 to about 30, alternatively about 15 to about 20, alternatively of about 18 grams in a 40 gram sample of the composition.

Embodiment 12 relates to the composition according to any one of the preceding embodiments, wherein the composition further comprises one or more lipids.

Embodiment 13 relates to the composition according embodiment 12, wherein the lipid is present in amount of about 5 to 12, alternatively of about 7 grams in a 40 gram sample of the composition.

Embodiment 14 relates to the composition according to any one of the preceding embodiments, wherein the composition further comprises carbohydrates.

Embodiment 15 relates to the composition according to any one of the preceding embodiments, wherein the composition further comprises essential amino acids and glutamine.

Embodiment 16 relates to the composition according to any one of the preceding embodiments, in combination with a pharmaceutical agent in a formulation or a kit for separate, sequential, or simultaneous administration.

Embodiment 17 relates to a food or beverage product comprising the composition according to any one of the preceding embodiments.

Embodiment 18 relates to the food or beverage product of embodiment 17, wherein the food or beverage product is provided in servings of about 40 grams dry weight.

Embodiment 19 relates to the food or beverage product of embodiment 18 wherein the food or beverage product comprises a formulation as recited in Table 2.

Embodiment 20 relates to a method of treating an animal's gastrointestinal tract, the method comprising administering an effective amount of the composition according to any one of the preceding embodiments to the animal.

Embodiment 21 relates to the method of embodiment 20, wherein the animal is a mammal.

Embodiment 22 relates to the method of embodiment 21, wherein the mammal is a human.

Embodiment 23 relates to the method according to any one of embodiments 20-22, wherein the method comprises healing and/or restoring health to the animal's gastrointestinal tract.

Embodiment 24 relates to the method according to any one of embodiments 20-23, wherein the composition is administered to the animal as part of an adjunct therapy.

Embodiment 25 relates to the method according to any one of embodiments 20-24, wherein the method comprises reducing gastrointestinal inflammation in the animal.

Embodiment 26 relates to the method according to any one of embodiments 20-25, wherein the method comprises restoring a gastrointestinal function to the animal.

Embodiment 27 relates to the method according to any one of embodiments 20-26, wherein the method is used in conjunction with another medical or pharmaceutical therapy.

Embodiment 28 relates to the method according to any one of embodiments 20-27, wherein the method comprises reducing pathogens resident in a large intestine of the animal's gastrointestinal tract.

Embodiment 29 relates to the method according to any one of embodiments 20-28, wherein the method comprises improving or enhancing a quality of the animal's life.

Embodiment 30 relates to the method according to any one of embodiments 20-29, wherein the animal is a human, and wherein the method comprises improving or enhancing a quality of the human's life per a validated or recognized clinical quality of life questionnaire.

Embodiment 31 relates to the method according to embodiment 30, wherein the validated or recognized clinical quality of life questionnaire is selected from DSFQ, GIQLI and IBDQ.

Embodiment 32 relates to the method according to any one of embodiments 20-31, wherein the method comprises enhancing a level of *Bifidobacterium* spp. in the animal.

Embodiment 33 relates to the method according to any one of embodiments 20-32, wherein the method comprises enhancing a level of butyrate in the animal.

Embodiment 34 relates to the method according to any one of embodiments 20-33, wherein the method comprises enhancing a level of *Faecalibacterium prausnitzii* in the animal.

Embodiment 35 relates to the method according to any one of embodiments 20-34, wherein the method comprises enhancing a level of *Roseburia* spp. in the animal.

Embodiment 36 relates to the method according to any one of embodiments 20-35, wherein administering the effective amount of the composition method is further defined as administering the effective amount of the composition prophylactically to ameliorate a GI-related condition in the animal, prevent an episodic symptom in the animal, and/or enhance a quality of life of the animal.

Embodiment 37 relates to the method according to any one of embodiments 20-36, wherein the method further comprises administering a composition that provides nutritional supplementation to the animal.

Embodiment 38 relates to the method according to any one of embodiments 20-37, wherein the method is used in a treatment of IBS in the animal.

Embodiment 39 relates to the method according to any one of embodiments 20-38, wherein the method is used in a treatment of IBD in the animal.

Embodiment 40 relates to the method according to any one of embodiments 20-39, wherein the method is used in a treatment of Celiac disease in the animal.

Embodiment 41 relates to the method according to any one of embodiments 20-40, wherein the method is used in a treatment of Ulcerative colitis in the animal.

Embodiment 42 relates to the method according to any one of embodiments 20-41, wherein the method is used in a treatment of Crohn's disease in the animal.

Embodiment 43 relates to a prebiotic composition for use in a method of reducing or suppressing inflammation in the gastrointestinal tract of a mammal, the prebiotic composition comprising a mixture of 2'fucosyllactose (2'FL) and isomaltooligosaccharide (IMO).

Embodiment 44 relates to embodiment 43, wherein the mixture comprises the 2'FL and the IMO in a ratio of 2'FL:IMO of about 1:1 to about 1:10.

Embodiment 45 relates to embodiment 44, wherein the ratio of 2'FL:IMO is about 1:2 to about 1:5.

Embodiment 46 relates to embodiment 45, wherein the ratio of 2'FL:IMO is about 1:2.5.

Embodiment 47 relates to embodiment 43, wherein the mixture comprises the 2'FL and the IMO in a ratio of 2'FL:IMO of 1:1 to 1:10.

Embodiment 48 relates to embodiment 47, wherein the ratio of 2'FL:IMO is 1:2 to 1:5.

Embodiment 49 relates to embodiment 48, wherein the ratio of 2'FL:IMO is 1:2.5.

Embodiment 50 relates to any one of embodiments 43-49, wherein the prebiotic composition comprises a supplemental nutrient mixture.

Embodiment 51 relates to embodiment 50, wherein the supplemental nutrient mixture comprises at least one of a vitamin, a mineral, fish oil, an omega fatty acid, a probiotic, a medical food, or any combination thereof.

Embodiment 52 relates to any one of embodiments 43-52, wherein the prebiotic composition is in the form of a dry food concentrate.

Embodiment 53 relates to embodiment 52, wherein the dry food concentrate is configured to provide at least 5% of a daily calorie requirement of a human.

Embodiment 54 relates to any one of embodiments 43-53, wherein the prebiotic composition comprises one or more components selected from the group consisting of flavorings, dyes, flow modifiers, preservatives, fillers, binders, and dispersing agents.

Embodiment 55 relates to any one of embodiments 43-54, wherein the prebiotic composition comprises one or more components selected from the group consisting of carbohydrates, nucleic acids, lipids, minerals, anabolic nutrients, vitamins, antioxidants, probiotic bacterial strains, and lipotropic agents.

Embodiment 56 relates to relates to any one of embodiments 43-55, wherein the mixture of 2'FL and IMO is a component of a medical food product.

Embodiment 57 relates to the embodiment 56, wherein the medical food product comprises at least one of a fat component, a lipid component, a protein source component, and a combination thereof.

Embodiment 58 relates to any one of embodiments 56-57, wherein the medical food product comprises about 2 grams of 2'FL and about 5 grams of IMO per approximately 40 gram dry weight serving of the medical food product.

Embodiment 59 relates to any one of embodiments 56-58, wherein the medical food product comprises from about 5 to about 12 grams of a fat or lipid component per approximately 40 gram dry weight serving of the medical food product.

Embodiment 60 relates to any one of embodiments 56-59, wherein the medical food product comprises from about 10 to about 30 grams of a protein source component per approximately 40 gram dry weight serving of the medical food product.

Embodiment 61 relates to the prebiotic composition according to any one of embodiments 1-19 for use in a method of treating one or more gastrointestinal disorders or diseases in a human patient.

Embodiment 62 relates embodiment 61, wherein the method of treating comprises increasing or stabilizing a level of butyrate in a large intestine of the human patient as compared to a baseline level of butyrate in a large intestine of the human patient taken prior to the treatment.

Embodiment 63 relates to any one of embodiments 61-62, wherein the method of treating comprises reducing a pathogen resident in the large intestine of the human patient.

Embodiment 64 relates to any one of embodiments 61-63, wherein the method of treating comprises increasing a level of *Bifidobacterium* spp. in the human patient as compared to a baseline of the level of *Bifidobacterium* spp. in the human patient taken prior to the treatment.

Embodiment 65 relates to any one of embodiments 61-64, wherein the one or more gastrointestinal disorders or diseases comprises Irritable Bowel Syndrome (IBS), Inflammatory Bowel Disease(s) (IBD), Crohn's disease, ulcerative colitis (UC), and/or celiac disease.

Embodiment 66 relates to any one of embodiments 61-65, wherein the method of treating comprises reducing and/or suppressing inflammation in the gastrointestinal tract of the human patient as compared to a baseline level of inflammation in the gastrointestinal tract of the human patient taken prior to the treatment.

Embodiment 67 relates to any one of embodiments 61-66, wherein the method of treating comprises improving the human patient's quality of life as determined according to one or more of the Digestive Symptom Frequency Questionnaire (DSFQ), the Gastrointestinal Quality of Life Index (GIQLI), and the Inflammatory Bowel Disease Questionnaire (IBDQ).

Embodiment 68 relates to any one of embodiments 61-67, wherein the method of treating comprises treating the human patient with one or more pharmaceutical therapies selected from the group consisting of mesalamines, sulphasalazines, 5-ASA agents, corticosteroids, anti-inflammatory medications, antibody therapies, drugs used against pain, diarrhea, and/or infections, and serotonin-4 receptor agonists.

Embodiment 69 relates to any one of embodiments 61-68, wherein the method of treating comprises bringing about an increase in a level of short chain fatty acids (SCFAs) in a large intestine of the human patient as compared to a baseline level of SCFAs in the large intestine of the human patient taken prior to the treatment.

Embodiment 70 relates to any one of embodiments 61-69, wherein the wherein the method of treating comprises bringing about an increase in a level of *Faecalibacterium prausnitzii* in the human patient's gastrointestinal tract as compared to a baseline level of *Faecalibacterium prausnitzii* in the human patient's gastrointestinal tract taken prior to the treatment.

Embodiment 71 relates to any one of embodiments 61-70, wherein the method of treating comprises bringing about an increase in a level of *Roseburia* spp. in the human patient's gastrointestinal tract as compared to a baseline level of *Roseburia* spp. in the human patient's gastrointestinal tract taken prior to the treatment.

Each aspect so defined may be combined with any other aspect or aspects of the embodiments of the invention. In particular, any feature indicated as being optional or advantageous may be combined with any other feature or features indicated as being optional or advantageous.

In an effort to further illustrate the embodiments herein, this disclosure includes the following non-limiting examples:

EXAMPLES

Exemplary Composition 1

A first composition comprising a combination of 2'fucosyllactose (2'FL) and isomaltooligosaccharide (IMO) is formulated as shown in Table 1 below to give a first prebiotic composition.

TABLE 1

| Exemplary Composition 1: | | | |
|---|---|---|---|
| Nutrient | Per Svg | Nutrient | Per Svg |
| Serving (Svg) Size (g) | 40 | Vitamin E (IU) | 7.5 |
| Servings Per Container | 14 | Thiamin (mg) | 0.375 |
| Calories (kcal) | 150 | Riboflavin (mg) | 0.425 |
| Total Fat (g) | 5 | Niacin (mg) | 5 |
| Saturated Fat (g) | 1.5 | Vitamin B6 (mg) | 0.5 |
| Trans Fat (g) | 0 | Folate (mcg) | 185.2 |

TABLE 1-continued

Exemplary Composition 1:

| Nutrient | Per Svg | Nutrient | Per Svg |
|---|---|---|---|
| Polyunsaturated Fat (g) | 1 | Vitamin B12 (mg) | 0.5 |
| Monounsaturated Fat (g) | 2 | Biotin (mcg) | 75 |
| Cholesterol (mg) | 0 | Pantothenic Acid (mg) | 2.5 |
| Sodium (mg) | 100 | Phosphorus (mg) | 185 |
| Potassium (mg) | 220 | Iodine (mcg) | 3.75 |
| Total Carbohydrate (g) | 17 | Magnesium (mg) | 35 |
| Dietary Fiber (g) | 7 | Zinc (mg) | 35 |
| Sugars (g) | 3 | Selenium | 52.5 |
| Protein (g) | 15 | Copper (mg) | 1.5 |
| Vitamin A (IU) | 1250 | Manganese (mg) | 1.5 |
| Amino Acid mg/Serving | | | |
| L-Alanine (mg) | 740 | L-Phenylalanine (mg) | 670 |
| L-Arginine (mg) | 1080 | L-Proline (mg) | 550 |
| L-Aspartic Acid (mg) | 1360 | L-Serine (mg) | 640 |
| L-Cystine (Cysteine) (mg) | 150 | L-Threonine (mg) | 470 |
| L-Glutamic Acid (mg) | 2050 | L-Tryptophan (mg) | 130 |
| L-Glutamine (mg) | 310 | L-Tyrosine (mg) | 490 |
| Glycine (mg) | 500 | L-Valine (BCAA) (mg) | 1190 |
| L-Histidine (mg) | 300 | L-Lysine (as L-lysine HCl) | 1650 |
| L-Isoleucine (BCAA) (mg) | 1070 | L-Methionine (mg) | 160 |
| L-Leucine (BCAA) (mg) | 1820 | | |

Dietary Fiber is a mixture of about 2 grams of 2'FL and about 5 grams of IMO per serving.

Exemplary Composition 2

A second composition comprising a combination of 2'FL and IMO is formulated as shown in Table 2 below to include flavorings (vanilla, and natural flavors), sweeteners (sugar), and supplemental nutrients to give a second prebiotic composition comprising a vanilla flavor.

Exemplary Composition 3

A third composition comprising a combination of 2'FL and IMO is formulated as shown in Table 2 below to include flavorings (cocoa powder, and natural flavors), sweeteners (sugar), and supplemental nutrients to give a third prebiotic composition comprising a chocolate flavor.

TABLE 2

Exemplary Compositions 2 and 3:

| Exemplary Composition 2 - Vanilla | Exemplary Composition 3 - Chocolate |
|---|---|
| Pea Protein Isolate | Pea Protein Isolate |
| Isomalto-Oligosaccharide | Isomalto-Oligosaccharide |
| Rice Protein Concentrate | Rice Protein Concentrate |
| 2'-Fucosyllactose Powder | 2'-Fucosyllactose Powder |
| Flaxseed | Golden Flaxseed |
| Organic Cane Sugar | Cane Sugar |
| Natural Flavors | Natural Flavors |
| High Oleic Sunflower Oil | Sunflower Oil |
| L-Lysine HCl | L-Lysine |
| Medium Chain Triglycerides | Medium Chain Triglycerides |
| L-Leucine | L-Leucine |
| Silica | Silica |
| L-Valine | L-Valine |
| L-Alanyl-L-Glutamine | L-Alanyl-L-Glutamine |
| L-Isoleucine | L-Isoleucine |
| Xanthan Gum | Xanthan Gum |
| Vitamin And Mineral Blend (Zinc Gluconate, Ascorbic Acid, Manganese Gluconate, D-Alpha Tocopheryl Acetate, Copper Gluconate, D-Biotin, Retinyl Palmitate, Niacinamide, Cholecalciferol, D-Calcium | Vitamin and Mineral Blend (Zinc Gluconate, Ascorbic Acid, Manganese Gluconate, D-Alpha Tocopheryl Acetate, Copper Gluconate, D-Biotin, Retinyl Palmitate, Niacinamide, Cholecalciferol, D-Calcium |

TABLE 2-continued

Exemplary Compositions 2 and 3:

| Exemplary Composition 2 - Vanilla | Exemplary Composition 3 - Chocolate |
|---|---|
| Pantothenate, Chromium Picolinate, Pyridoxine HCl, Riboflavin, Potassium Iodide, Thiamin HCl, Calcium L-5-Methyltetrahydrofolate, Selenomethionine, and Methylcobalamin) | Pantothenate, Chromium Picolinate, Pyridoxine HCl, Riboflavin, Potassium Iodide, Thiamin HCl, Calcium L-5-Methyltetrahydrofolate, Selenomethionine, and Methylcobalamin) |
| Luo Han Guo Fruit (Monk Fruit) Extract | Luo Han Guo Fruit (Monk Fruit) Extract |
| Vanilla | Dutch Processed Cocoa Powder |
| Rosemary Extract | Rosemary Extract |

General Treatment Example 1

Most data below are expressed as "mean±SD." Changes from baseline to 6 weeks were analyzed using two-sided paired t-tests. Gut microbiota PCR data were log-transformed prior to analysis. A value of $p<0.05$ is considered statistically significant.

The prebiotic composition of Exemplary Composition 1 is formulated into a medical food formulated to provide nutritional support in the management of compromised gut function, mucosal inflammation, malnutrition, and/or intestinal dysbiosis. The medical food is then administered to adult human patients with previously diagnosed IBS, IBD, and/or celiac disease. The effects of the prebiotic composition on GI symptoms and quality of life in the adult human patients is then measured to determine the effects of the prebiotic composition on GI symptoms and quality of life in adults with previously diagnosed IBS, IBD, and celiac disease.

Example 1A—Clinical Study 12 adult participants, including seven men and five women ranging in age from 22-60 years old (mean age of 31.4±10.5) with a mean weight of 162.8±33.1 lbs and a mean BMI of 23.8±3.4 $kg/m^2$ completed the study. These participants were recruited via U.S. medical, osteopathic, and naturopathic practices. Each participant had a previous diagnosis of IBS, UC, Crohn's disease, or celiac disease. Each participant consumed 1 serving (approximately 40 grams) of Exemplary Composition 1, which was formulated as a medical food mixed with water, twice daily for 6 weeks. As each serving of Exemplary Composition 1 includes about 2 grams of 2'FL and about 5 grams of IMO, each patient was treated daily with about 4 grams of 2'FL and about 10 grams of IMO.

Example 1B—Improved Quality of Life Per GIQLI

At the beginning of the study and at the study end, participants completed the Gastrointestinal Quality of Life Index (GIQLI), a validated 36-item questionnaire designed for patients with disorders of the esophagus, stomach, gallbladder, pancreas, small intestine, colon, and rectum (i.e., GI conditions/disorders) The GIQLI yields a total score and 4 subdomain scores, and detects changes over time: higher scores are consistent with a better quality of life.

Example 1C—Improved Quality of Life of US Sufferers Per DSFQ for UC

Participants with UC (n=4) were asked to complete condition-specific questionnaires, including the Digestive Symptom Frequency Questionnaire (DSFQ) if they also had IBS, the Quality of Life in Inflammatory Bowel Disease Questionnaire (IBDQ) if they had UC or Crohn's disease.

Example 1D—Improved Quality of Life for Patients Suffering for IBD Per IBDQ

The four participants with UC also completed the Inflammatory Bowel Disease Questionnaire (IBDQ) which yields a total score and four subdomain scores. The total score improved by a mean of 43.6% (p=0.078) following treatment with the oligosaccharide prebiotic, and the systemic symptoms subdomain score improvement of 66.9% was statistically significant (p=0.0002). The IBDQ scores are indicative of an improvement in the quality of life of the participants.

Example 1E—Improved Quality of Life for Patients Suffering for IBS Per DSFQ

The seven participants with IBS also completed the Digestive Symptom Frequency Questionnaire (DSFQ) and indicated a minor improvement in mean score by 10.3% (p=0.522).

Example 1F—Improved GI Health Compared to Healthy Individuals Per Patient's Stool Samples Stool samples were collected at both baseline and also at the end of the study. These stool samples were analyzed using the GENOVA GI EFFECTS® Comprehensive Stool Profile to assess gut microbiota short-chain fatty acid (SCFA) levels, biomarkers that indicate digestive and absorptive function, gut inflammation, and immunology, and to identify species that may be classified as "potential pathogens." The results of these analyses are summarized in FIGS. 1 and 2.

Figure 1B:
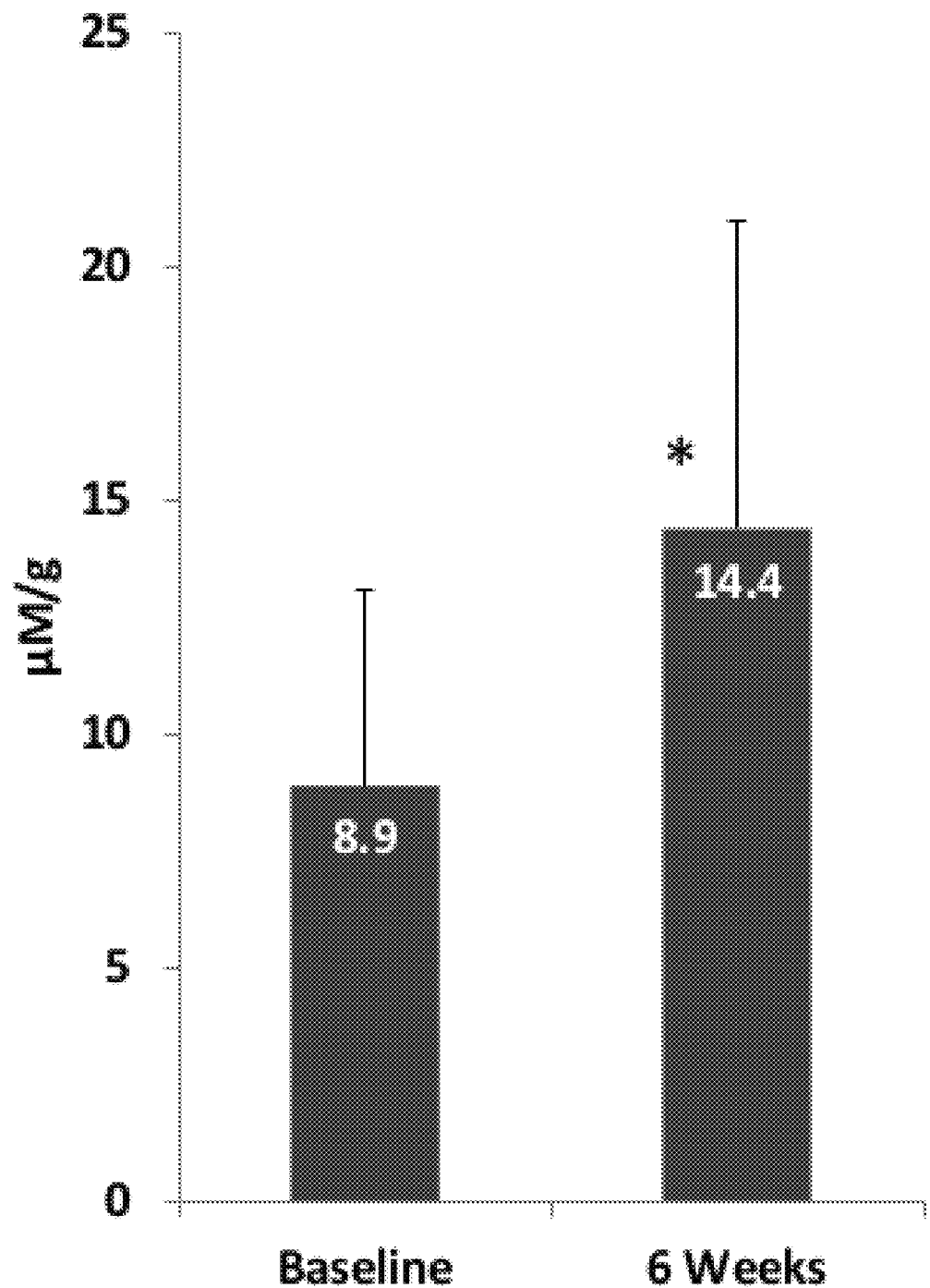
FIG. 1B is a bar chart illustrating the amount of butyrate in the Total SOFA illustrated in FIG. 1A.
Figure 2:
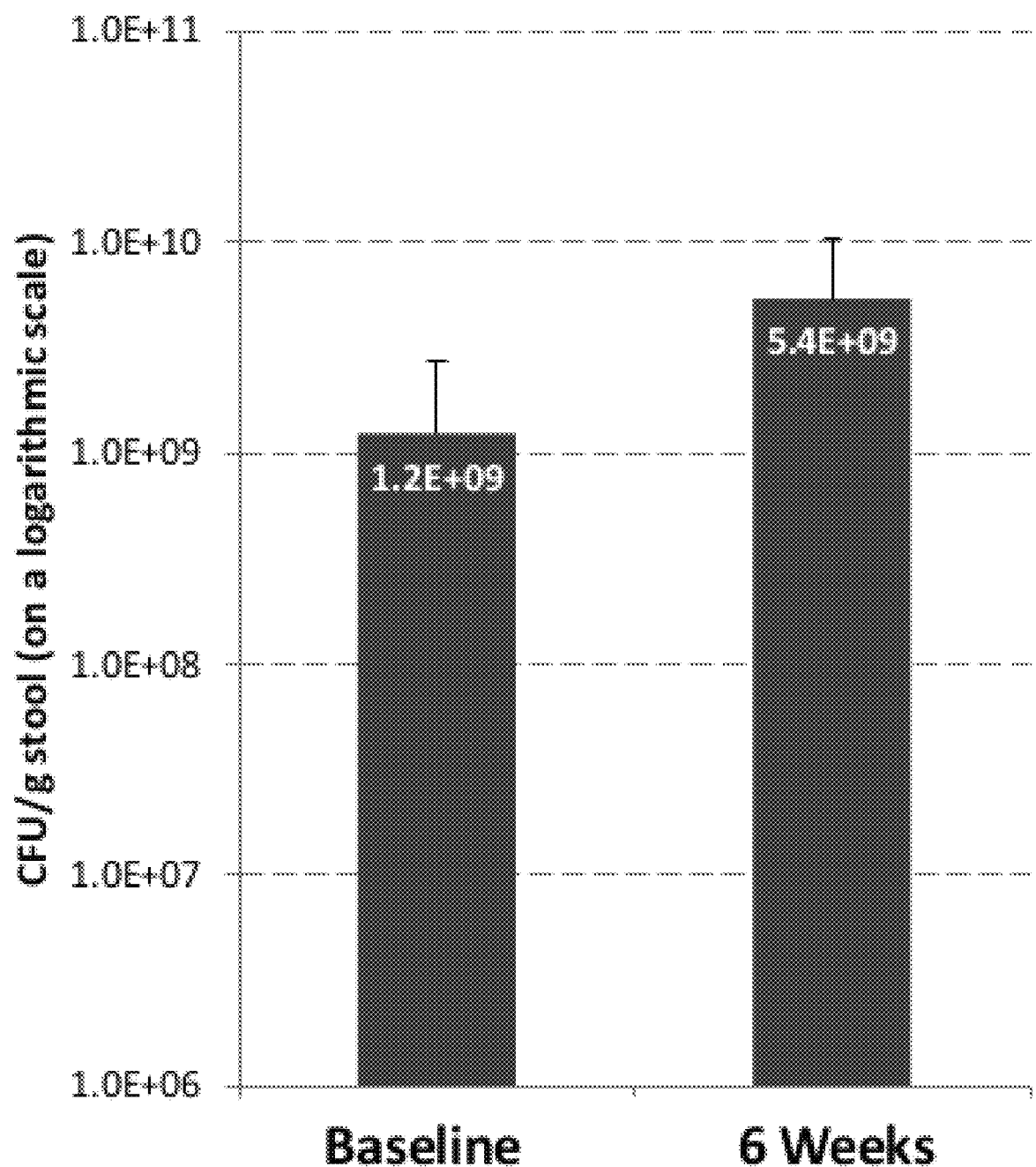
FIG. 2 is a bar chart illustrating levels of *Bifidobacterium* spp. at baseline and 6 weeks after treatment with the prebiotic composition according to Example 1. Paired t-test was conducted on log-transformed data. *p<0.05.

More specifically, the data in FIGS. 1 and 2 demonstrate that administration of the prebiotic composition, as described above, increases both production of SCFAs (including butyrate, see FIG. 1B) and also levels of *Bifidobacterium* in human subjects.

As shown in FIGS. 1A and 1B in particular, administering the prebiotic composition (Exemplary Composition 1) according to the method exemplified in Example 1 increases butyrate levels by a mean of 72.7% (p=0.022), and increases total SCFA levels by a mean of 72.2% (p=0.026) after 6 weeks.

As shown in FIG. 2 in particular, administering the prebiotic composition (Exemplary Composition 1) according to the method exemplified in Example 1 increases Levels of *Bifidobacterium* spp. by 336.9% (p=0.028) after 6 weeks.

Without being bound to any specific mechanism of action, it is hypothesized that the mechanism for the increased production of SCFAs, including butyrate, the increased levels of *Bifidobacterium*, and the resolution of potentially pathogenic microorganisms involves the induction of intestinal microbiota changes by the synergistic combination of 2'FL and IMO in the prebiotic composition, as described above.

Out of the 12 participants that completed the study, a total of 8 potential pathogens were identified at baseline. At the end of the study, 7 of the 8 total potential pathogens were no longer detected. In contrast, only 2 potential pathogens were present at the end of the study. (data not shown)

Overall—GI Symptoms and GI Quality of Life Scores Improved

All participants, regardless of pre-existing conditions, completed the GIQLI. The resulting GIQLI scores are shown in Table 3 below.

TABLE 3

GIQLI scores at baseline and 6 weeks among participants who completed the study:

| | Scores | Mean % change | P value | Score range |
|---|---|---|---|---|
| Total score | Baseline: 94.3 ± 25.5<br>6 weeks: 109.4 ± 19.2 | 20.8% | 0.020 | 0-144 |
| | Subdomain | | | |
| GI symptoms | Baseline: 53.3 ± 10.3<br>6 weeks: 61.4 ± 7.7 | 18.1% | 0.022 | 0-76 |
| Social function | Baseline: 10.7 ± 3.8<br>6 weeks: 12.3 ± 3.7 | 18.4% | 0.004 | 0-16 |
| Emotional function | Baseline: 12.0 ± 5.8<br>6 weeks: 14.7 ± 4.5 | 46.5% | 0.139 | 0-20 |
| Physical function | Baseline: 15.6 ± 7.4<br>6 weeks: 17.8 ± 6.1 | 36.5% | 0.164 | 0-28 |

As shown in Table 3, total scores improved by a mean of 20.8% (p=0.020) from baseline to the end of the study. Scores for the GI symptoms domain and the social function domain also improved significantly.

Summary of Example 1 Results

The clinical study described above demonstrates that the embodiments herein have the following unexpected effects when used in the treatment of a group of adult humans with IBS, IBD, and/or celiac disease:

Reduced GI symptoms and improved overall GI quality of life;

Total Gastrointestinal Quality of Life Index (GIQLI) questionnaire scores improved by 16.0% (p=0.020);

GIQLI GI symptoms sub-domain scores improved by 15.2% (p=0.022);

Increased production of short chain fatty acids (SCFAs) including butyrate. Butyrate, a hallmark of GI health, increased significantly by 72.7% (p=0.022), while total SCFAs increased by 72.2% (p=0.026) (as illustrated in FIG. 1);

Levels of *Bifidobacterium* spp. increased by 336.9% (p=0.028) (as illustrated in FIG. 2);

Levels of other known butyrate producing gut bacteria increased: *Faecalibacterium prausnitzii* increased by 60.7% (p=0.086) and *Roseburia* spp. increased by 135.3% (p=0.072) (data not shown);

Resolved potential pathogenic intestinal microflora; and 87.5% of potential pathogens that were identified at baseline had resolved by the end of the study.

Example 2

A specific adult male with irregular symptoms of wasting, including a BMI of 17, participated in the clinical study of Example 1. By the end of the study, the irregular symptoms reported at the beginning of the trial had resolved, and the specific adult male had gained 9 pounds. Though the trial had concluded, the specific adult male sought to continue the use of the embodiment, as he had not experienced weight gain in a very long time.

The examples shown above are not exhaustive, but are intended to provide guidance sufficient to practice the embodiments herein.

With regard to the description herein, where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit and an upper limit, is disclosed, any number falling within the range is specifically disclosed. In particular, the following numbers within the range are specifically disclosed: for example, when a variable ranges from 1 percent to 100 percent, this disclosure explicitly includes 1 percent, 2 percent, 3 percent, 4 percent, 5 percent, . . . 50 percent, 51 percent, 52 percent, . . . , 95 percent, 96 percent, 97 percent, 98 percent, 99 percent, or 100 percent. Moreover, any ratio, expressed as a range defined by two numbers as each number, and variations between listed whole numbers is also specifically disclosed. Use of the term "optionally" with respect to any element of the embodiment, whether included in a claim or not means that the element is required, or alternatively, the element is not required, both alternatives being within the scope of the invention. Use of broader terms such as comprises, includes, and having should be understood to provide support for narrower terms such as consisting of, consisting essentially of, and comprised substantially of.

Additionally, any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Likewise, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

Lastly, it is to be understood that the appended claims are not limited to express and particular compounds, compositions, or methods described in the detailed description, which may vary between particular embodiments which fall within the scope of the appended claims. As such, with respect to any Markush groups relied upon herein for describing particular features or aspects of various embodiments, different, special, and/or unexpected results may be obtained from each member of the respective Markush group independent from all other Markush members. Each member of a Markush group may be relied upon individually and or in combination and provides adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of embodiments and independent and dependent claims, including those related to or dependent on single and/or multiple embodiments and claims, are herein expressly contemplated.

The invention claimed is:

1. A prebiotic composition comprising an oligosaccharide component comprising a combination of 2'fucosyllactose (2'FL) and isomaltooligosaccharide (IMO) in a weight ratio of about 1:2.5, wherein the 2'FL is present in an amount of from 4 to 6 weight percent (wt. %) and the IMO is present in an amount of from 10 to 15 wt. %, each based on the total dry weight of a serving of the prebiotic composition, and wherein the serving is adapted to be consumed by a human selected from the group consisting of adults and juveniles.

2. The prebiotic composition of claim 1, wherein the serving is about 40 grams dry weight.

3. The prebiotic composition of claim 1, wherein the prebiotic composition is in the form of a dry powder adapted to be dissolved in at least one of water and a consumable liquid or mixed with a foodstuff.

4. The prebiotic composition of claim 1, further comprising at least one additive comprising: (i) an amino acid; (ii) a peptide; (iii) a protein; (iv) a lipid; (v) a vitamin; (vi) a carbohydrate; (vii) a nucleic acid; (viii) a mineral; (ix) an anabolic nutrient; (x) an antioxidant; (xi) a probiotic bacterial strain; (xii) a lipotropic agent; or (xiii) any combination of (i) to (xii).

5. The prebiotic composition of claim 4, wherein the at least one additive comprises the (i) amino acid, the (ii) peptide, and/or the (iii) protein, and wherein the at least one additive is present in an amount of from 10 to 30 grams, optionally in an amount of from 15 to 20 grams, optionally in an amount of 18 grams, per 40 gram dry weight sample of the prebiotic composition.

6. The prebiotic composition of claim 4, wherein the prebiotic composition comprises the lipid, and wherein the lipid is present in an amount of from 5 to 12 grams, optionally an amount of 7 grams, per 40 gram dry weight sample of the prebiotic composition.

7. The prebiotic composition of claim 1, further comprising: (i) a flavoring agent; (ii) a dye; (iii) a flow modifier; (iv) a preservative; (v) a filler; (vi) a binder; (vii) a dispersing agent; or (viii) any combination of (i) to (vii).

8. A foodstuff or beverage comprising the prebiotic composition of claim 1, wherein the prebiotic composition is present in an amount of about 40 grams dry weight per serving of the foodstuff or beverage.

9. The foodstuff or beverage of claim 8, further comprising: (i) a fat component; (ii) a lipid component; (iii) a protein source component; or (iv) any combination of (i) to (iii).

10. The foodstuff or beverage of claim 9, comprising: (i) 2 grams of 2'FL and 5 grams of IMO; and at least one of: (ii) from 5 to 12 grams of the fat component; (iii) from 5 to 12 grams of the lipid component; (iv) from 10 to 30 grams of the protein source component; or (v) any combination of (ii) to (iv); each based on a 40 gram dry weight sample of the foodstuff or beverage.

11. The foodstuff or beverage of claim 8, wherein the foodstuff or beverage is further defined as a medical food.

12. The prebiotic composition of claim 1, wherein the 2'FL is present in an amount of from 4.5 to 5.5 wt. %, and the IMO is present in an amount of from 12 to 13 wt. %, each based on the total weight of the serving of the prebiotic composition.

13. The prebiotic composition of claim 1, further comprising a fat and/or lipid component in an amount of from 12.5 to 30 wt. % based on the total weight of the prebiotic composition, and further comprising a protein component in an amount of from 25 to 75 wt. %, optionally of from 35 to 50 wt. %, based on the total weight of the serving of the prebiotic composition.

14. The prebiotic composition of claim 1, wherein the oligosaccharide component consists essentially of 2'FL and IMO.

15. A kit comprising a combination of the prebiotic composition of claim 1 and a pharmaceutical agent, optionally wherein the pharmaceutical agent comprises: (i) mesalamine; (ii) sulphasalazine; (iii) a 5-ASA agent; (iv) a corticosteroid; (v) an anti-inflammatory medication; (vi) an antibody therapeutic agent; (vii) a drug used against pain, diarrhea, and/or infection; (viii) a serotonin-4 receptor agonist; or (ix) any combination of (i) to (viii).

16. A prebiotic composition in the form of a dry powder adapted to be dissolved in at least one of water and a consumable liquid, wherein:
the prebiotic composition comprises:
an oligosaccharide component consisting of a combination of 2'fucosyllactose (2'FL) and isomaltooligosaccharide (IMO) in a weight ratio of about 1:2.5;
a lipid component;
a protein source component; and
at least one additive component other than an oligosaccharide;
the 2'FL is present in an amount of from 4.5 to 5.5 weight percent (wt. %), the IMO is present in an amount of from 12 to 13 wt. %, the lipid component is present in an amount of from 12.5 to 30 wt. %, and the protein source component is present in an amount of from of from 35 to 50 wt. %, each based on the total weight of the prebiotic composition; and
after consumption, the prebiotic composition ameliorates a gastrointestinal (GI) condition in an adult or a juvenile.

17. The prebiotic composition of claim 16, in the form of a serving having a dry weight of about 40 grams, wherein the serving comprises: about 2 grams of 2'FL and about 5 grams of IMO; from 5 to 12 grams of the lipid component; from 10 to 30 grams of the protein source component; and from 15 to 20 grams of the additive component; provided the total weight of the serving is about 40 grams dry weight.

18. A method of ameliorating a gastrointestinal (GI) condition in a human, comprising administering to the human the prebiotic composition of claim 1; wherein the human is selected from the group consisting of adults and juveniles.

19. The method of claim 18, wherein the GI condition is selected from: (i) irritable bowel syndrome (IBS); (ii) an inflammatory bowel disease (IBD); (iii) Celiac disease; (iv) ulcerative colitis; (v) Crohn's disease; or (vi) any combination of (i) to (v).

20. The method of claim 18, further defined as: (i) healing or restoring health to a GI tract of the human; (ii) reducing or suppressing inflammation in a GI tract of the human; (iii) restoring a GI function in the human; (iv) reducing an amount of a pathogen present in a large intestine of the human; (v) improving or enhancing a quality of life of the human; or (vi) any combination of (i) to (v).

21. The method of claim 18, further defined as increasing a level of (i) *Bifidobacterium* spp.; (ii) *Faecalibacterium prausnitzii*; (iii) *Roseburia* spp.; or (iv) any combination of (i) to (iii), in a GI tract of the human.

22. The method of claim 18, further defined as: (i) increasing or stabilizing a level of butyrate; (ii) increasing a level of short chain fatty acids (SCFAs); or (iii) both (i) and (ii), in a large intestine of the human.

23. The method of claim 18, wherein the prebiotic composition is administered to the human as: (i) a foodstuff or beverage; (ii) a medical food; (iii) a nutritional supplement; (iv) a combination with a pharmaceutical agent; or (v) any combination of (i) to (iv).

* * * * *